(12) United States Patent
Kim et al.

(10) Patent No.: US 11,454,794 B2
(45) Date of Patent: Sep. 27, 2022

(54) SYSTEMS AND METHODS FOR CONDUCTING CONTACT-FREE THICKNESS AND REFRACTIVE-INDEX MEASUREMENTS OF INTRAOCULAR LENSES USING A SELF-CALIBRATING DUAL CONFOCAL MICROSCOPY

(71) Applicant: The United States of America, as represented by the Secretary, Department of Health and Human Services, Silver Spring, MD (US)

(72) Inventors: Do-Hyun Kim, Clarksville, MD (US); Ilko Kolev Ilev, Rockville, MD (US); Robert Harold James, Gaithersburg, MD (US); Don Calogero, Montgomery Village, MD (US)

(73) Assignee: The United States of America, as represented by the Secretary, Department of Health and Human Services, Silver Spring, MD (US)

( * ) Notice: Subject to any disclaimer, the term of this patent is extended or adjusted under 35 U.S.C. 154(b) by 271 days.

(21) Appl. No.: 16/913,803

(22) Filed: Jun. 26, 2020

(65) Prior Publication Data

US 2020/0326520 A1    Oct. 15, 2020

Related U.S. Application Data

(62) Division of application No. 15/904,916, filed on Feb. 26, 2018, now Pat. No. 10,712,545.

(Continued)

(51) Int. Cl.
  *G02B 21/06* (2006.01)
  *G02B 21/00* (2006.01)
  (Continued)

(52) U.S. Cl.
  CPC .............. *G02B 21/06* (2013.01); *G01B 11/06* (2013.01); *G01N 21/41* (2013.01);
  (Continued)

(58) Field of Classification Search
  CPC .... G02B 21/06; G02B 21/16; G02B 21/0032; G02B 21/002; G02B 21/0076;
  (Continued)

(56) References Cited

U.S. PATENT DOCUMENTS 5,074,642 A    12/1991  Hicks
5,304,810 A    4/1994   Amos
  (Continued)

OTHER PUBLICATIONS

Ilev, "A simple confocal fibre-optic laser method for intraocular lens power measurement," *Eye*, 21:819-823 (Jul. 2007).
(Continued)

*Primary Examiner* — William R Alexander
*Assistant Examiner* — Tamara Y. Washington
(74) *Attorney, Agent, or Firm* — Klarquist Sparkman, LLP (57) ABSTRACT

Systems and methods for conducting contact-free thickness and refractive-index measurements of transparent objects, such as intraocular lenses using a dual confocal microscopy system are disclosed.

11 Claims, 9 Drawing Sheets

Related U.S. Application Data (60) Provisional application No. 62/467,849, filed on Mar. 7, 2017.

(51) Int. Cl.
*G02B 21/02* (2006.01)
*G02B 21/18* (2006.01)
*G01N 21/41* (2006.01)
*G01B 11/06* (2006.01)
*A61F 2/16* (2006.01)

(52) U.S. Cl.
CPC ......... *G02B 21/0032* (2013.01); *G02B 21/02* (2013.01); *G02B 21/18* (2013.01); *A61F 2/16* (2013.01); *A61F 2240/008* (2013.01); *G01N 2021/4126* (2013.01)

(58) Field of Classification Search
CPC ...... G02B 21/082; G02B 21/24; G02B 21/22; G02B 21/365; G02B 21/0088; G02B 21/361; G02B 21/0012; G02B 21/00; G02B 21/0024; G02B 21/32; G02B 21/08; G02B 21/20; G02B 21/02; G02B 21/367; G02B 2027/0134; G01N 21/6458; G01N 21/6419; G01N 21/6421; G01N 21/648; G01N 21/6408; G01N 21/6428; G01N 2001/284; A61B 1/00186; A61B 1/0638; A61B 90/20; A61B 3/132; A61B 5/0066; A61F 9/007
See application file for complete search history.

(56) References Cited

U.S. PATENT DOCUMENTS

| | | | |
|---|---|---|---|
| 5,442,573 | A | 8/1995 | Bredberg et al. |
| 7,068,878 | B2 | 6/2006 | Crossman-Bosworth et al. |
| 7,285,089 | B2 | 10/2007 | Viellerobe et al. |
| 7,719,668 | B2 | 5/2010 | Ilev |
| 8,254,020 | B2 | 8/2012 | Holy et al. |
| 8,290,358 | B1 | 10/2012 | Georgiev |
| 10,061,111 | B2 | 8/2018 | Hillman |
| 10,712,545 | B2 * | 7/2020 | Kim ................. G02B 21/06 |
| 10,962,755 | B2 * | 3/2021 | Kapanidis ............ G02B 21/361 |
| 11,169,366 | B2 * | 11/2021 | Kapanidis .......... G02B 21/0088 |
| 11,179,028 | B2 * | 11/2021 | Tearney .................. A61B 1/041 |
| 11,300,774 | B2 * | 4/2022 | Dickensheets ....... A61B 5/0077 |
| 2001/0048082 | A1 | 12/2001 | Osipchuk et al. |
| 2003/0021016 | A1 | 1/2003 | Grier |
| 2003/0142934 | A1 | 7/2003 | Pan et al. |
| 2006/0011804 | A1 | 1/2006 | Engelmann et al. |
| 2006/0182320 | A1 | 8/2006 | Peszynski et al. |
| 2007/0052958 | A1 | 3/2007 | Ulrich et al. |
| 2007/0272842 | A1 | 11/2007 | Knebel et al. |
| 2010/0280315 | A1 | 11/2010 | Pan |
| 2011/0121202 | A1 | 5/2011 | Li et al. |
| 2012/0140240 | A1 | 6/2012 | Hillman et al. |
| 2012/0277288 | A1 | 11/2012 | Drumm et al. |
| 2014/0146376 | A1 | 5/2014 | Kleppe et al. |
| 2016/0327779 | A1 | 11/2016 | Hillman |
| 2018/0259759 | A1 | 9/2018 | Kim et al. |

OTHER PUBLICATIONS

Ilev et al., "Dual-confocal fiber-optic method for absolute measurement of refractive index and thickness of optically transparent media," *Optics Letters*, 27(19):1693-1695 (Oct. 1, 2002).

Ilev et al., "Innovative confocal laser method for exact dioptric power measurement of intraocular lens implants," *Chinese Optics Letters*, 6(12):876-878 (Dec. 10, 2008).

Kim et al., "Advanced confocal microscope using single hollow-core photonic bandgap fibre design," *Electronics Letters*, 43(11):608-609 (May 24, 2007).

Kim et al., "Fiberoptic Confocal Microscopy Using a 1.55-μm Fiber Laser for Multimodal Biophotonics Applications," *IEEE Journal of Selected Topics in Quantum Electronics*, 14(1):82-87 (Jan./Feb. 2008).

Kim et al., "Simple confocal thickness gauge based on fibre-optic confocal sensor for non-contact measurement," *Electronics Letters*, 46(24):1594-1595 (Nov. 25, 2010).

Kim et al., "Upconversion fiber-optic confocal microscopy under near-infrared pumping," 33(5):425-427 (Mar. 1, 2008).

\* cited by examiner

SYSTEMS AND METHODS FOR CONDUCTING CONTACT-FREE THICKNESS AND REFRACTIVE-INDEX MEASUREMENTS OF INTRAOCULAR LENSES USING A SELF-CALIBRATING DUAL CONFOCAL MICROSCOPY

CROSS-REFERENCE TO RELATED APPLICATIONS

This application is a divisional of U.S. patent application Ser. No. 15/904,916, filed Feb. 26, 2020, which claims the benefit of U.S. Provisional Application No. 62/467,849, filed Mar. 7, 2017, both of which are incorporated by reference herein in their entirety.

FIELD

The present disclosure relates generally to systems and methods for conducting contact-free thickness and refractive-index measurements of intra-ocular lenses, and in particular to a self-calibrating dual confocal microscopy system for conducting such contact-free thickness and refractive index measurements.

BACKGROUND

The development and use of intraocular lenses ("IOL") for refractive cataract surgery has changed the life of cataract patients and has become more popular since the first implantation of such lenses in 1949. Among many of the physical parameters that determine the characteristics and quality of an intraocular lens, focal length (or dioptric power), modular-transfer function ("MTF"), astigmatism, thickness, and refractive index play important roles. MTF, astigmatism, and dioptric power can be measured using commercially available IOL-characterization equipment. However, in spite of their significance in the characterization of intraocular lenses, thickness and refractive index of an intraocular lens have not been precisely measured by users. It has been found that the thickness of an intraocular lens cannot be accurately measured by simple mechanical devices, such as calipers or micrometers, since these mechanical devices can affect the optical quality of the intraocular lens since such a method requires that the intraocular lens be brought into direct physical contact by these mechanical devices during measurement. In addition, the curvature of the intraocular lens itself can raise difficulties for obtaining precise thickness measurements. As such, there is a need for determining the precise thickness and refractive index of an intraocular lens that does not require direct contact with the intraocular lens.

SUMMARY

In an embodiment, a dual confocal microscopy system having a first confocal microscope in alignment with a second confocal microscope. The dual confocal microscopy system may further include a light source for transmitting a first laser beam in which a fiber optic coupler splits the first laser beam into a first divided laser beam and a second divided laser beam. The fiber optic coupler defines a first pathway for transmitting the first divided laser beam and a second pathway for transmitting the second divided laser beam. In addition, the first confocal microscope is in operative communication with the first pathway for launching the first divided laser beam to the first confocal microscope, wherein the first confocal microscope may include a first collimating lens for transforming first divided laser beam into a plurality of first collimated laser beams and a first focusing lens having a first focal length for focusing the plurality of first collimated laser beams. Similarly, the second confocal microscope is in operative communication with the second pathway for launching the second divided laser beam to the second confocal microscope, wherein the second confocal microscope may include a second collimating lens for transforming the second divided laser beam into a plurality of second collimated laser beams and a second focusing lens having a second focal length for focusing the plurality of second collimated laser beams. In one arrangement, the first confocal microscope and the second confocal microscope are longitudinally aligned along a beam axis as defined by the first pathway and the second pathway. A detector is in operative communication with the fiber optic coupler for detecting peak intensities of a plurality of signals generated by the first divided laser beam and the second divided laser beam detected by the detector In another embodiment, a method for noncontact measurement of an object may include: aligning a first confocal microscope with a second confocal microscope along a longitudinal beam axis; positioning an object having a first reflective side and an opposite second reflective side between the first confocal microscope and the second confocal microscope; measuring the first reflective side of the object by the first confocal microscope at a first position and measuring the second reflective side of the object by the second confocal microscope at a second position; and calibrating the first confocal microscope and the second confocal microscope based on the measurements of the first reflective side and the second reflective side at the first and second positions.

Additional objectives, advantages and novel features are set forth in the description which follows and/or will become apparent to those skilled in the art upon examination of the drawings and detailed description which follows.

Corresponding reference characters indicate corresponding respective elements among the views of the drawings. The headings used in the figures should not be interpreted to limit the scope of the claims.

DETAILED DESCRIPTION

As described herein, a dual confocal microscopy system is used to conduct contact-free thickness and refractive-index measurements of transparent objects, such as intraocular lenses. The system employs a method based on measurements of confocal defocus of the reflection of light beams from the opposite surfaces of the transparent object to accurately measure shape, thickness, and transparency of the transparent object.

Referring to the drawings, various embodiments of the dual confocal microscopy system are illustrated and generally indicated as 100 in FIGS. 1-11. In one embodiment shown in FIG. 1, the dual confocal microscopy system 100 may include a first confocal microscope 101 which is in alignment with a second confocal microscope 103 for each receiving respective laser beams 105 launched from a laser source 102 for performing contact-free thickness and refractive index measurements of an object. The laser source 102 launches the laser beam 105 into a fiber optic coupler 104, such as a 50:50 fiber optic coupler, having a first arm 106 in operative communication with the first confocal microscope 101 and a second arm 108 in operative communication with the second confocal microscope 103. The fiber optic coupler 104 divides the laser beam 105 into a first laser beam 105A, which is launched through the first arm 106 and a second laser beam 105B, which is launched through the second arm 108. In one arrangement, the first arm 106 of the fiber optic coupler 104 defines a first pathway that transmits the first laser beam 105A to the first confocal microscope 101, while the second arm 108 of the fiber optic coupler 104 defines a second pathway that transmits the second laser beam 105B to the second confocal microscope 103. The dual arrangement of a first confocal microscope 101 in alignment with the second confocal microscope 103 along the same longitudinal beam axis 300 allows for reflection of the divided first and second laser beams 105A and 105B from opposite surfaces of an object being measured, thereby allowing the measurement of the object without limits related to shape, thickness, and transparency as shall be discussed in greater detail below.

Figure 1:
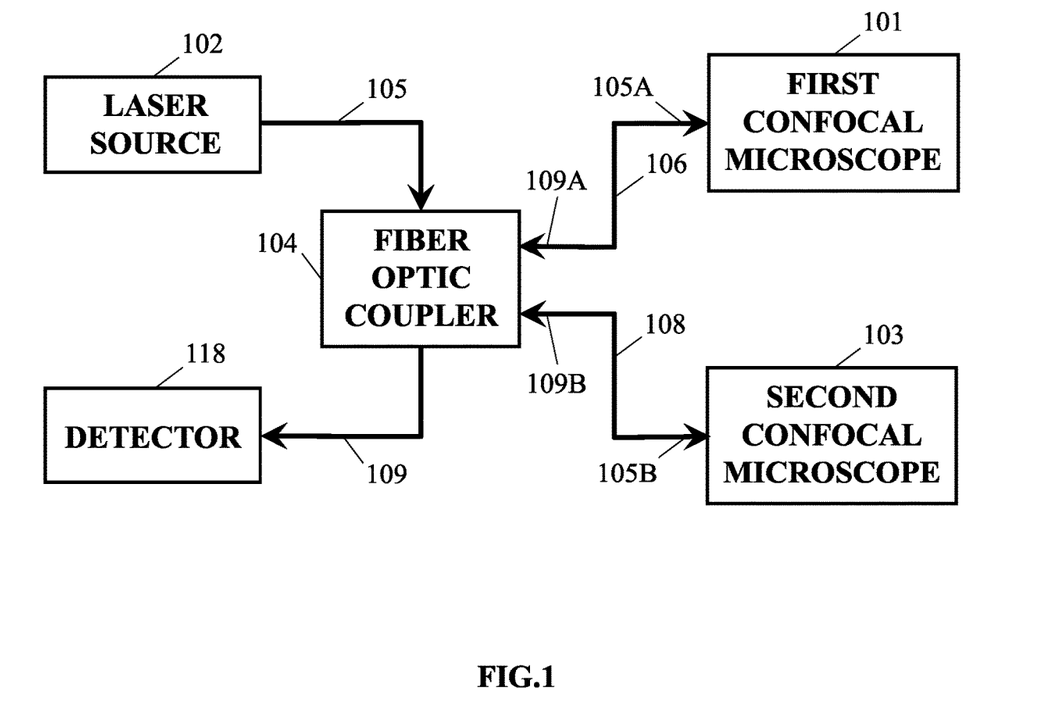
FIG. 1 is a simplified illustration of an embodiment of a dual confocal microscopy system.
Figure 2:
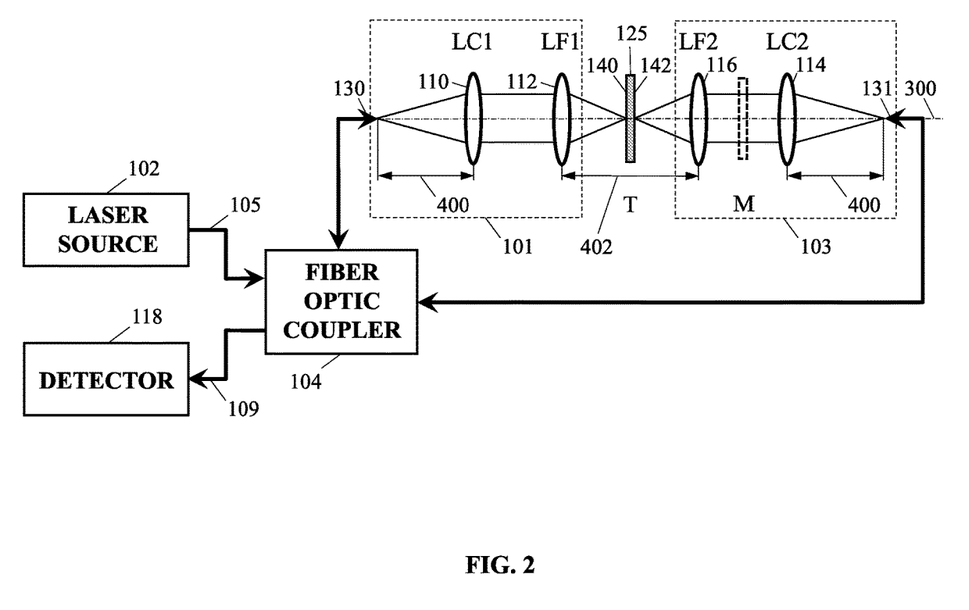
FIG. 2 is a simplified illustration showing one arrangement for the dual confocal microscopy system.
Figure 3:
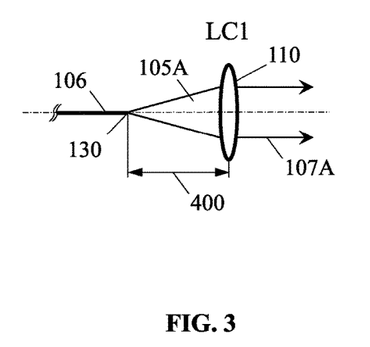
FIG. 3 is a simplified illustration showing the collimation of one of the divided laser beams.

Referring to FIGS. 2 and 3, in one arrangement the first confocal microscope 101 may include a first collimating lens 110 in which the first divided laser beam 105A launched from the first arm 106 of the fiber optic coupler 104 is collimated into a plurality of first collimated laser beams 107A. Similarly, the second confocal microscope 103 may include a second collimating lens 114 in which the second laser beam 105B transmitted from the second arm 108 of the fiber optic coupler 104 is collimated into a plurality of second collimated laser beams 107B.

Figure 4:
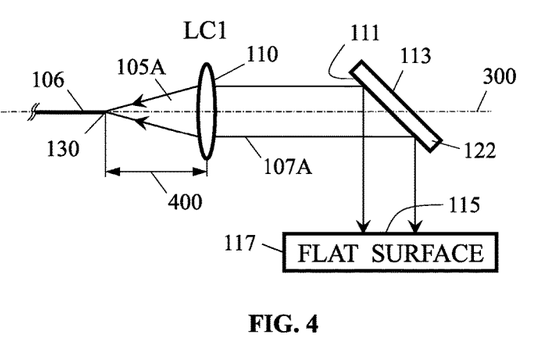
FIG. 4 is a simplified illustration showing one arrangement for conducting an initial alignment of one of the confocal microscopes.

Referring to FIG. 4, by way of example, the first confocal microscope 101 may be initially aligned relative to the first arm 106 by positioning a flat total-reflectance mirror 122 having a first reflective surface 111 such that the first collimated beams 107A are reflected onto an object 117 having a flat surface 115. The flat mirror 122 is oriented at substantially a 45 degree angle relative to the beam axis 300 such that an image is formed onto the flat surface 115. Adjusting the orientation of the first collimating lens 110 makes the image either smaller or larger, thereby indicating whether the collimated laser beams 107A are substantially aligned along beam axis 300. The same operation is then performed with the second confocal microscope 103 such that the opposite reflective surface 113 of the flat mirror 122 is used to align the second collimated laser beams 107B is also substantially aligned with the same beam axis 300 as a reference. Once the initial alignment operation is completed, the first and second microscopes 101 and 103 may be further aligned with beam axis 300.

Figure 5:
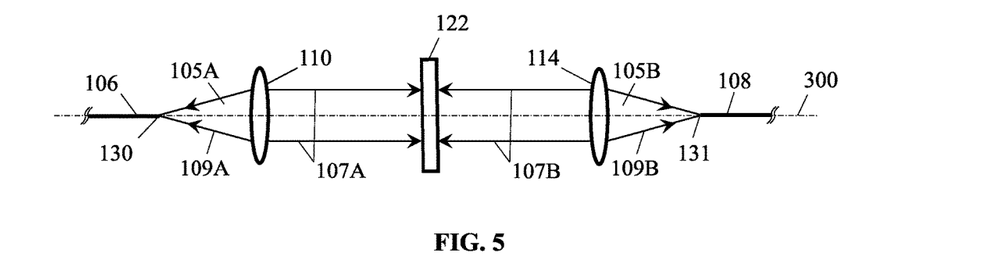
FIG. 5 is a simplified illustration showing another arrangement for conducting an alignment of one of the confocal microscopes.

Referring to FIG. 5, further alignment of the first and second confocal microscopes 101 and 103 relative to the beam axis 300 may be performed using the same arrangement shown in FIG. 4 with the flat mirror 122 oriented at a 90 degree or perpendicular angle relative to the beam axis 300 such that the first reflective surface 111 is perpendicular to the plurality of first collimated laser beams 107A. When the plurality of first collimated laser beams 107A reflect off the first reflective surface 111 of the flat mirror 122, a plurality of first reflected laser beams 109A is generated which follow an identical or substantially identical path back through the first collimated lens 110. The first collimated lens 110 focuses the plurality of collimated reflected laser beams 109A back through the first arm 106 for detection by detector 118. In one aspect, the distance 400 (FIG. 3) between the aperture 130 of the first arm 106 and the collimated lens 110 may be adjusted to achieve optimal alignment of the first microscope 101 relative to beam axis 300 by observing an image that represents the intensity of the peak generated by the collimated reflected laser beams 109A detected by the detector 118. For example, the better the alignment of the collimated reflected laser beams 109A relative to the beam axis 300, the more intense the peak detected by the detector 118. Accordingly, the optimal distance 400 between the first collimated lens 110 and the emitter 130 of the first arm 106 may be determined that allows optimal alignment of the plurality of collimated reflected laser beams 109A relative to the beam axis 300.

The same alignment procedure is conducted for the second confocal microscope 103 such that the second collimated lens 114 is positioned at the optimal distance 400 from the emitter 131 of the second arm 108, thereby aligning the plurality of collimated reflected laser beams 109B with the beam axis 300. In this manner, the first and second confocal microscopes 101 and 103 of the dual confocal microscopy system 100 are brought into alignment with same beam axis 300.

Referring back to FIG. 2, once the first and second confocal microscopes 101 and 103 are aligned relative to beam axis 300, the first and second focusing lenses 112 and 116 are both positioned relative to the first and second collimated lenses 110 and 114, respectively, at a respective first position. As shown, the object 125 with a known thickness as defined between the first and second reflective surfaces 111 and 113 is positioned equidistant between the first and second focusing lenses 112 and 116. The plurality of collimated reflected laser beams 109A and 109B reflect off the object 122 and are detected by detector 118 such that the position of the peaks having a maximum signal intensity generated by the collimated reflected laser beams 109A and 109B are detected. Once the position of the peaks with maximal signal intensity was determined for an object 125 of known thickness, then this calibration of the dual confocal microscopy system 100 allows the thickness of an object 125 of known thickness to be measured based on the calibration of the first and second confocal microscopes 101 and 103 for the object 125 with known thickness that was previously measured.

In one arrangement, the dual confocal microscopy system 100 comprises the same arrangement illustrated in FIGS. 1-5. The distance between the first and second confocal microscopes 101 and 103 was effectively the same distance between first and second focusing lenses 112 and 116, which depends on the working distance (WD) of the first and second focusing lens 112 and 116, which are identical, and the unknown thickness of the object 125 to be measured. For example, when first and second focusing lenses 112 and 116 are identical 20×(NA−0.40, WD=3.3 mm), the distance between the first and second focusing lenses 112 and 116 must be larger than 7.6 mm) (1 mm+3.3 mm+3.3 mm) to measure the thickness of about 1 mm. In some embodiments, the most conventional method is to position the first and second focusing lenses 112 and 116 is as far apart as possible within the travel limit of the mechanical stages 126 and 128 on which the object to be measured is mounted and translated along beam axis 300; however, the farther apart the first and second focusing lenses 112 and 116 are, the more time is required to take measurements of the object 125 by the dual confocal microscopy system 100.

In some embodiments, the laser source 102 may be a solid state diode laser with a center wavelength of 658 nm, output power of 25 mW, and a beam diameter of 8.0 mm. In some embodiments, the collimating lenses 110 and 114 are identical 10×(NA=0.25) objective lenses. In some embodiments, the focusing lenses 112 and 116 are identical 20×(NA=0.40; WD=3.3 mm) objective lenses. Although the above are exemplary components of the first and second confocal microscopes 101 and 103, other types of lasers and lenses may be used to construct the dual confocal microscopy system 100.

Figure 6:
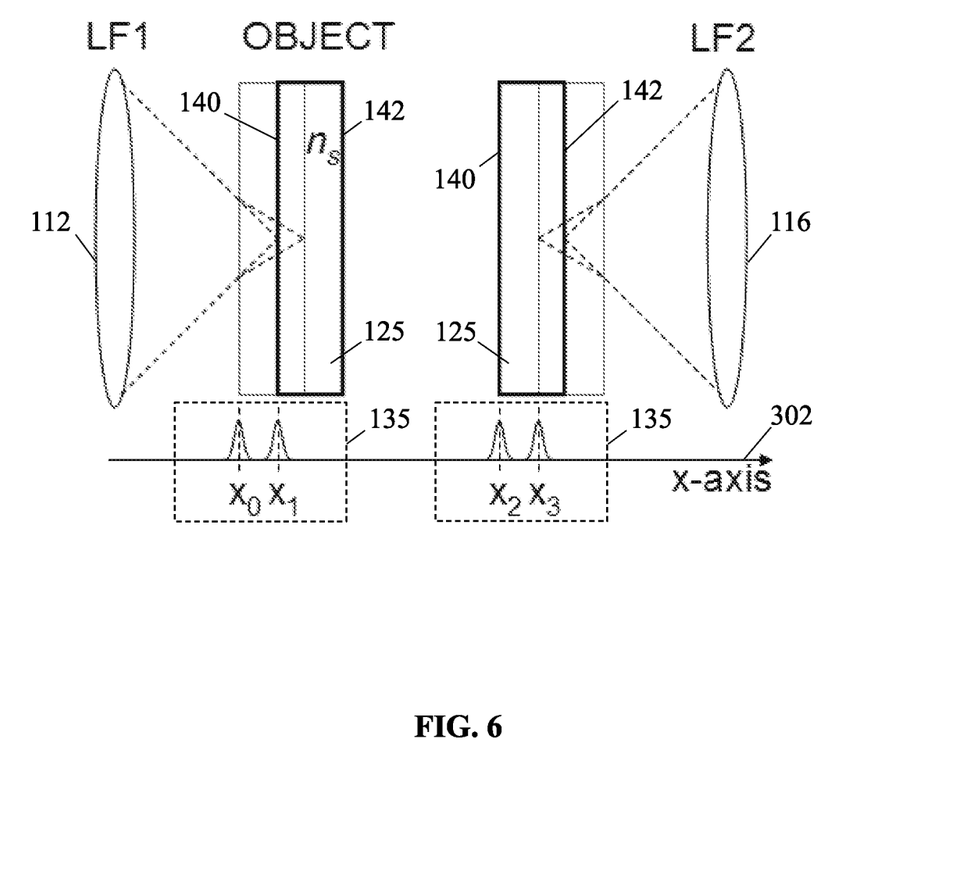
FIG. 6 is a simplified diagram illustrating one method for measuring refractive index using the dual confocal microscopy system.
Figure 7:
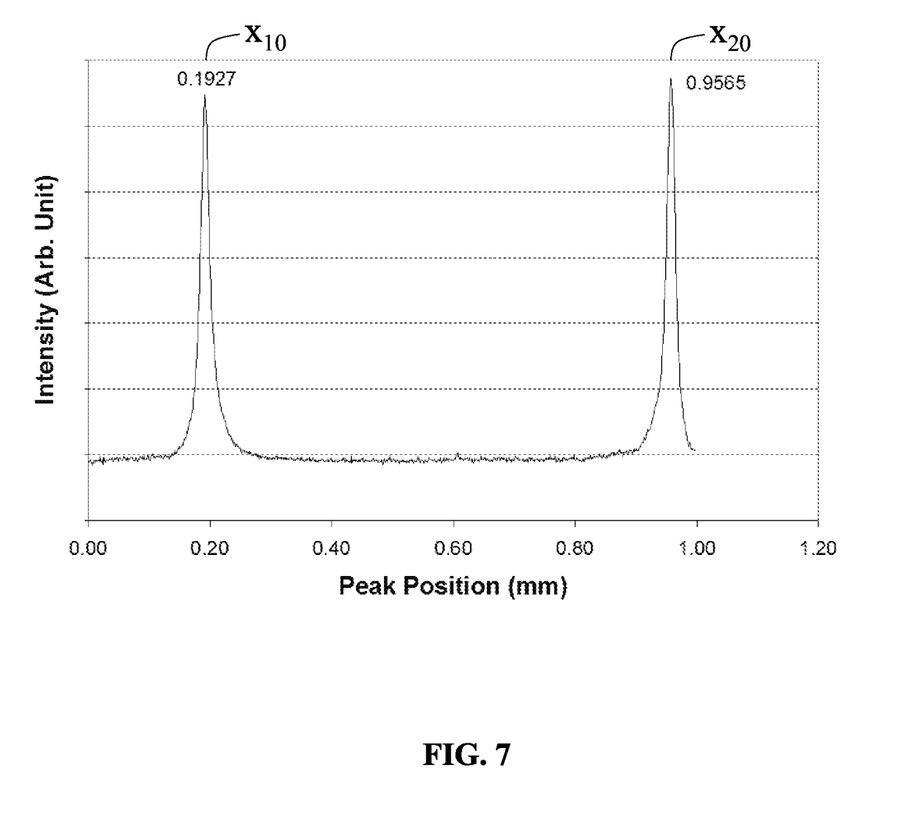
FIG. 7 is a graph showing the confocal reflection intensities for a thickness measurement of a standard 1 mm plate using a 20× objective lens.
Figure 8:
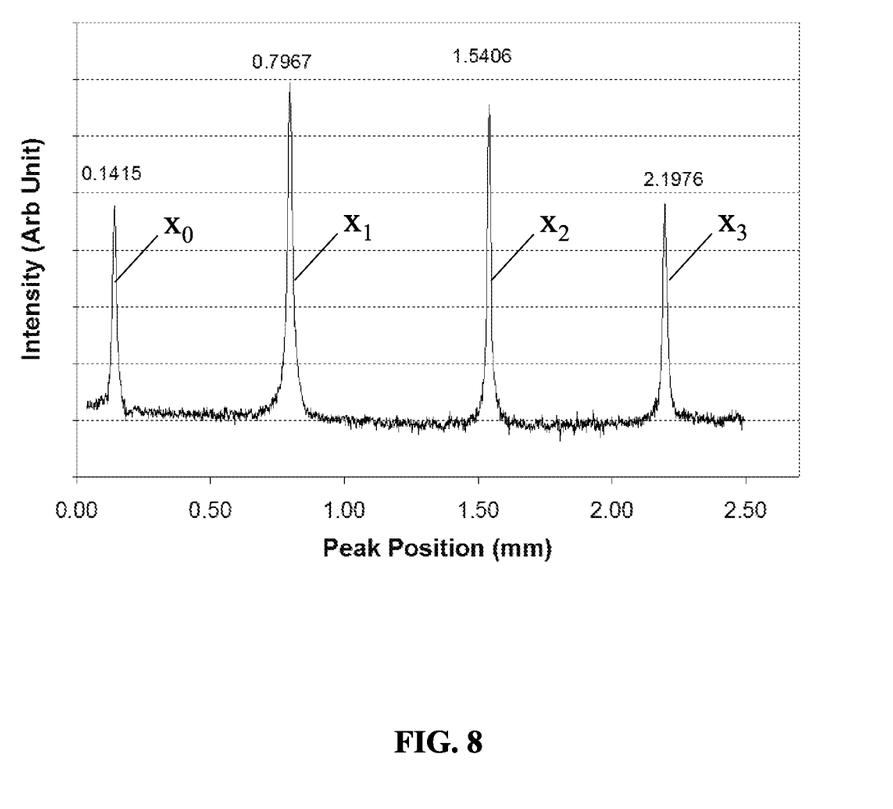
FIG. 8 is a graph showing the confocal reflection intensities for a thickness measurement of a glass plate using the 20× objective lens.

Referring back to FIGS. 2 and 6, the basic principle of operation of one embodiment of the dual confocal microscopy system 100 will be discussed in greater detail. In one embodiment, the distance between the first and second focusing lenses 112 and 116 may be length 402 and an object 125 having opposite parallel surfaces 140 and 142 with a certain degree of reflectivity which may be positioned between the first and second focusing lenses 112 and 116. In this embodiment, the thickness of the object 125, t0, is known to a high degree. The reflective parallel surfaces 140 and 142 of the object 125, such as a thin plate, may be aligned to be normal to the beam axis 300 using the alignment procedure discussed above. In some embodiments, the object 125 may be mounted on a mechanical stage 135, which moves along an x-axis 302. In operation, the travel distance of the object 125 along the x-axis 302 was limited between a first position in close proximity with the first focusing lens 112 and a second position in close proximity with the second focusing lens 116. The first and second reflected laser beams 109A and 109B focused by the respective first and second focusing lenses 112 and 116 were recorded while the object 125 was moved from the left side (e.g., closest to the first focusing lens 112) to the right side (e.g., closest to the second focusing lens 116). In some embodiments, the detector 118 may include a silicon photodiode combined with an analog-to-digital converter to detect the reflected laser beams 109A and 109B. Referring to FIGS. 7 and 8, it was found that if the object 125 was not transparent, there was one peak detected by the detector 118 (FIG. 2) when the left reflective surface 140 of the object 125 is at a position x10, wherein the left reflective surface 140 of the object 125 is a focal length of the first focusing lens 112, designated F1, away from the first focusing lens 112. As further shown, another peak was observed at position x20, when the right reflective surface 142 is a focal length of the second focusing lens 142, designated F2, away from the second focusing lens 116.

The distance between the first and second focusing lenses can be expressed in the following terms:

$$L=F1+1x20-x101+t0+F2 \tag{1}$$

When we repeat the same procedure using an object 125 with unknown thickness (t0), the maximum intensity peaks will be observed at x1 and x2, Equation (1) may now be expressed in the following terms:

$$L=F1+1x2-x11+ts+F2 \tag{2}$$

By comparing equations (1) and (2), we obtain an expression for unknown thickness ts in terms of known and measured parameters:

$$ts=t0+1x20-x101-1x2-x11 \tag{3}$$

Equation (3) suggests that the thickness of an object of unknown thickness can be measured, which as well defined reflecting surface on both sides, after calibrating the distance 402 between optical components using an object, such as a plate, of known thickness. In addition, this method does not require precise determination of the focal lengths of the first and second focal lenses 112 and 116 and the distance 402 between first and second focal lenses 112 and 116. It has been observed that two more peaks representing detected intensity peaks when a transparent object with a thickness smaller than the working distance between the first and second focal lenses 112 and 116 is used. Referring to FIG. 6, there is a back reflection when the right reflective surface of the object 125 at position x0. This is due to focusing the collimated light beams 105A and 105B through the transparent object 125. However, x0 is not is away from x1, since the refractive index of the object (ns) increases the effective focal length of the first focal lens 112. If d is designated as the distance between position x0 and position x1, the refractive index of the transparent object 125 can be calculated using other parameters:

$$ns=[NA2+(1-NA2)(ts/d)2]^{1/2} \tag{4}$$

As further shown in FIG. 6, another intensity peak is observed at x3 can also be used for the calculation by letting d be the distance between positions x2 and x3. This is true only when an object measured has inversion symmetry.

The thickness measurement of an intraocular lens requires another step for aligning the microscopy system 100. Unlike a parallel plate, an intraocular lens is required to be oriented normal to the beam axis 300, but it also requires the center of the intraocular lens to coincide with the beam axis 300 since the center is the thickness portion regardless of whether the intraocular lens has a plano-convex configuration or double-convex configuration. In addition, thickness measurement of a negative power intraocular lens is also possible.

After alignment of first and second collimating lenses 110 and 114, a flat total-reflectance mirror was positioned at location M and oriented to be normal to the beam axis 300. Location M is approximately a focal length of the intraocular lens away from location T. Using one of the first or second confocal microscopes 101 or 103, the dioptric power of the intraocular lens may be measured by positioning the intraocular lens at location T. This method provides not only a high precision measurement of the dioptric power of the intraocular lens, but also ensures the alignment of the intraocular lens relative to the beam axis 300. After the power measurement is made, the mirror at location M is removed and the first and second focusing lenses 112 and 116 are positioned at LF1 and LF2 locations. The remainder of the measurement procedure is the same as that for a parallel plate. The refractive index of the intraocular lens can be measured when the thickness of the intraocular lens is smaller than the WD of the first and second focusing lenses 112 and 116; however, the measured values using (x1−x0) and (x3−x2) are different when a plano-convex intraocular lens is used.

FIG. 7 shows an example of signals generated by the collimated reflected laser beams 109A and 109B when detected by detector 118 measured for a 1-mm standard metal plate with a 20× objective lenses. As noted above, 10× and 20× objective lenses were 0.1927 mm and 0.9565 mm, respectively. The full-width at half-maximum (FWHM) of a peak was 15 μm and the precision of a mechanical translational stage 135 used to longitudinally translate the metal plate was 0.1 μm. The FWHM of the dual confocal microscopy system 100 was larger than the theoretically predicted value, 3.5 μm, which is calculated using an expression for axial response of either the first or second confocal microscope 101 or 103 $(\Delta z)^{1/2}$:

$$(\Delta z)^{1/2} = 0.44 \lambda / (1 - \cos \alpha)$$

wherein $\lambda$ is the laser wavelength and $\sin \alpha$ is the numerical aperture of the first and second focusing lenses 112 and 116. The arrangement of the dual confocal microscopy system 100 showed lower axial resolution than theoretically predicted value due to the fact that the arrangement was operated under fiber-dominated mode for increased coupling efficiency by using larger NA (0.25) of the first and second collimating lenses 110 and 114 than that of an optical fiber (0.12).

FIG. 8 shows the measured data for a thin glass plate using a 20× objective lenses. The thickness of the glass plate was 1.00 mm when measured with a vernier caliper. Four peaks showing the intensity of each peak generated by the detected collimated reflected laser beams 109A and 109B were observed as the thickness of the glass plate is smaller than the WD of the first and second focusing lenses 112 and 116. The peaks at positions x0, x1, x2, and x3 were measured to be 0.1415 mm, 0.7968 mm, 1.5406 mm, and 2.1976 mm, respectively. The thickness and the refractive index of the glass plate can be calculated using equations (3) and (4): wherein is is 1.0199 mm and nx is 1.482 mm. Both test results match well with known values. The calculated values of d from (x1−x0) and (x3−x2) were 0.6552 mm and 0.6570 mm, respectively. The difference is 1.8 μm and is well within the experimental error. The peak intensities at x0 and x3 were smaller than those at x1 and x2 because the direct reflection from the front surface of the glass plate is stronger than the back surface of the glass plate.

Figure 9:
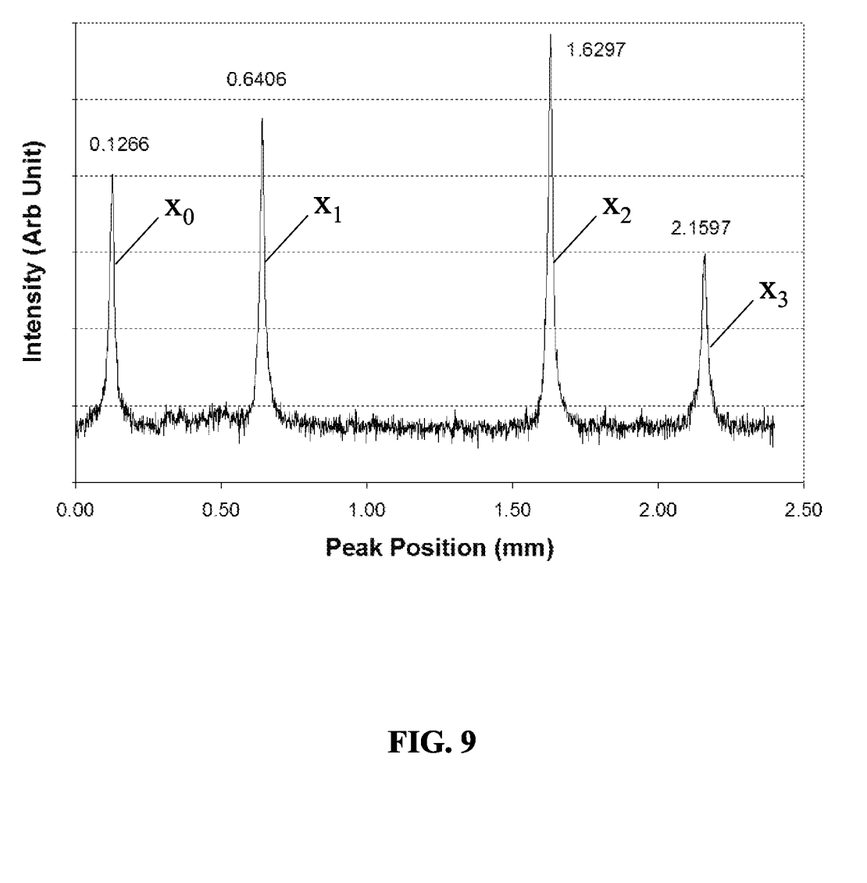
FIG. 9 is a graph showing the confocal reflection intensities for a thickness measurement of an intra-ocular lens using the 20× objective lens.

FIG. 9 shows the measured data for a plano-convex intraocular lens using a 20× objective lenses with a planar surface facing the first focusing lens 112. The thickness of the intraocular lens was 0.76 mm when measured with a vernier caliper. As shown, four peaks at positions x0, x1, x2 and x3 were measured to be 0.1266 mm, 0.6406 mm, 1.6297 mm, and 2.1697 mm. The thickness and the refractive index calculated using equations (3) and (4) were 0.7747 mm and 1.438 mm, respectively. Both test results match well with known values. The calculated values of d from (x1−x0) and (x3−x2) were 0.5140 mm and 0.5300 mm, respectively. The difference is 16 μm and is larger than the difference measured from the glass plate. It is due to the fact that the collimated reflected laser beams 109 measured from the first focusing lens 112 at location LF1 (peaks at positions x0 and x1) are through the planar surface; however, the reflected laser beams 109 measured from the second focusing lens 116 (peaks at positions x2 and x3) are through the convex surface of the intraocular lens. An additional focusing effect from the convex surface shortens the effective focus of the second focusing lens 116 at LF2, thus the peak was observed when the intraocular lens was closer to the second focusing lens 116 at location LF2 which generates a larger value of (x3−x2) than (x1−x0). In the test, (x1−x0) was used as d for the calculation of the refractive index. The intensity peak detected at x3 was also smaller than the intensity peak detected at x0. It was assumed that the convex surface of the intraocular lens is locally flat when it is at the laser focus (e.g., focal spot diameter is 1.5 μm). The dioptric power of the intraocular lens, which as measured during the alignment, was 26.7.

Figure 10:
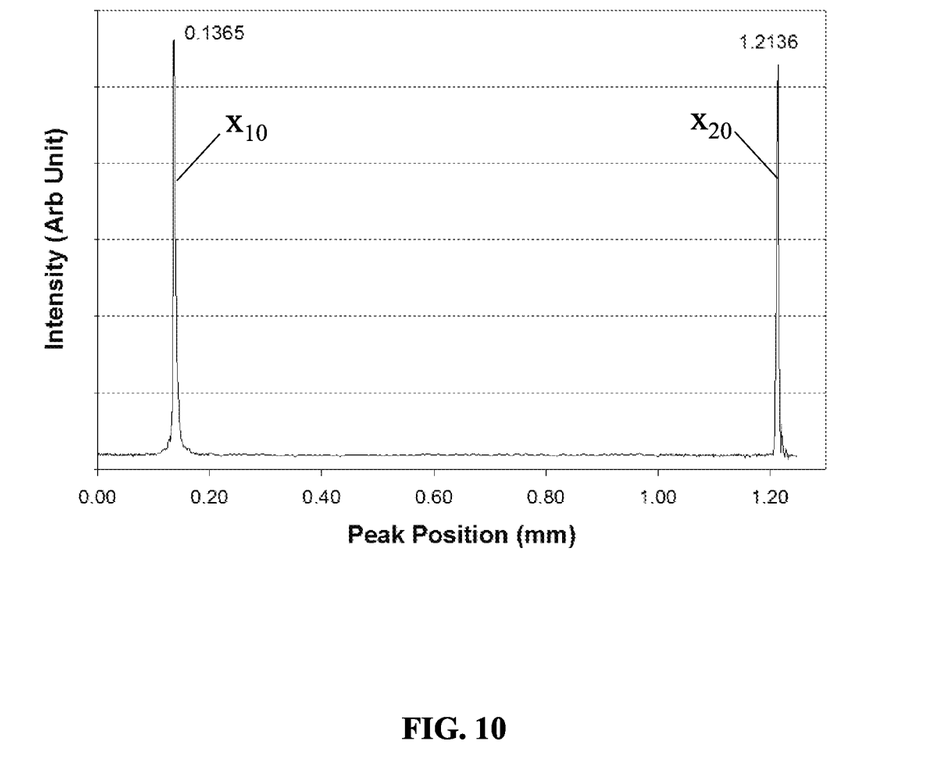
FIG. 10 is a graph showing the confocal reflection intensities for a thickness measurement of a standard 1 mm plate using a 60× objective lens.
Figure 11:
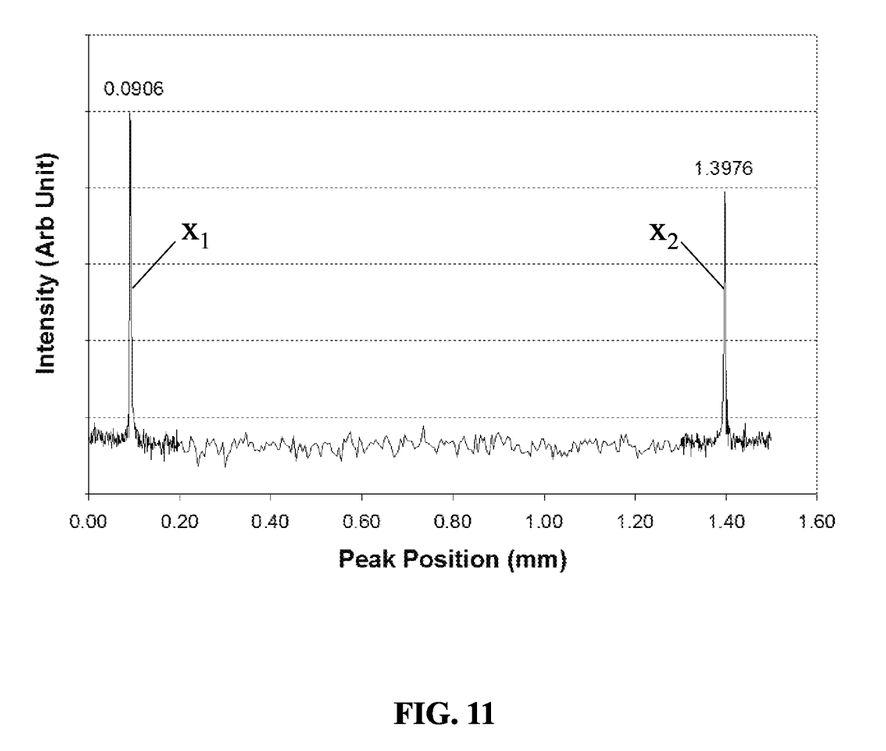
FIG. 11 is a graph showing the confocal reflection intensities for a thickness measurement of an intra-ocular lens using a 60× objective lens.

For comparison, a measurement was performed using a 60× objective lenses for the first and second focusing lenses 112 and 116. FIG. 10 shows the measured data for a standard 1-mm metal plate. As shown, the intensity peaks detected by detector 118 at x10 and x20 were 0.1365 mm and 1.2136 mm, respectively. Because of the high NA of the first and second focusing lenses 112 and 116, FWHM was reduced to 5 μm. FIG. 11 shows the measured data for the same intraocular lens in which x1 and x2 were measured to be 0.0906 mm and 1.3976 mm, respectively. The calculated thickness of the intraocular lens was 0.7700 mm, which is closer to the value measured with a vernier caliper than when the same lens was measured with a 20× objective lenses. Since the WD of the 60× objective lens is only 0.28 mm, the refractive index could not be measured. The objective lenses with a high NA and long WD, such as infinity-corrected lenses, can be used when the refractive index is measured while maintaining the high degree of accuracy is required.

A few factors that limit the accuracy of the whole measurement method will be discussed. The most import factor that affects the accuracy of the dual confocal microscopy system 100 is the alignment of the optical arrangement (e.g., collimating and focusing lenses). By following the alignment procedure discussed above, any inaccuracy attributable to misalignment was eliminated. In addition, it was found that the further accuracy may be expected when the detector 118 with higher sensitivity is used and mechanical optical mounts for orientation of optical components are provided. Once the dual confocal microscopy system 100 is aligned and calibrated, the measurement of thickness, refractive index and the intraocular lens dioptric power is repeatable at that calibration and measured accuracy each time a measurement is performed.

It has also been found that significant errors in F1 and F2 may be introduced when their values are determined solely by a single confocal signal; however, the present method eliminates the necessity of measuring F1 and F2 during the calibrating procedure using an object of known thickness to calibrate the dual confocal microscopy system 100. As such, any remaining errors from the alignment procedure may be cancelled out.

It has been found that axial resolution of an optical microscope system, whether a wide-field microscope or a confocal microscope laser scanning microscope, is less than the lateral resolution of the same system. Thus, accuracy of the measurement by using our method is inherently limited.

It was discovered that performance could be improved by using a shorter wavelength laser source and higher NA objective lenses. An improvement beyond the discussed limit is expected when white-light interferometric confocal microscope is used; however, the method is not valid for the measurement of the intraocular lens in which the alignment of the center of the intraocular lens to the beam axis is critical. An optical coherence tomographic method does not provide any higher than a confocal microscopic method, not to mention such a method cannot be used to measure the thickness of non-transparent objects.

Mechanical translational stage must have positional resolution smaller than FWHM of an axial confocal signal, and must provide high repeatability for optimal operation of the invention. Moreover, the possible error from the mechanical translational stage is not an accumulative value, and therefore accuracy remains the same regardless of the thickness of the sample being measured. This is true as the tested method eliminates one source of possible inaccuracy, L, by calibrating the dual confocal microscopy system 100 using a standard plate of known thickness. Any error induced from thermal expansion of the plate made of stainless steel is recognized. However, linear thermal expansion coefficient of stainless steel is 17.3×10−6/K at room temperature, which means the error due to thermal expansion is negligible considering the possible errors that can be induced by axial resolution of a conventional confocal microscope.

In conclusion, a novel dual confocal microscopy system was tested for employing a method of noncontact high-precision measurement of thickness for an object with reflective surfaces. We discovered that this method proved to be particularly useful for the thickness measurement of an intraocular lens in which contact-less measurement is highly desirable. Based on the foregoing tests, the Applicants were able to successfully measure the thickness of an intraocular lens with an accuracy as high as 0.0005 mm, when single mode fibers, 60× objective lenses, and a 658 nm laser light source were used. Because the alignment of the optical components of the dual confocal microscopy system is critical to the method, the Applicants developed a step-by-step procedure for the alignment of the optical components to reduce any potential errors due to misalignment. The measured thickness of 0.7700 mm, agrees with the value measured using a conventional mechanical device, such as a caliper. In addition, the refractive index of an intraocular lens was also measured using a 20× objective lenses in which the measured value obtained was 1.438 mm. The method works well with an object of any thickness or transparency as long as the thickness is within the travel limit of the mechanical translational stage and the object has a measurable back-reflection at its surfaces. In addition to the high precision of the method, measurements can be performed without any physical contact with the sample, which means the sample can be preserved in its original status. As such, fragile or soft material can also be used of the thickness measurement.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

The invention claimed is:

1. A method for noncontact measurement of an object comprising:
   aligning a first confocal microscope with a second confocal microscope along a beam axis;
   positioning an object having a first reflective side and an opposite second reflective side between the first confocal microscope and the second confocal microscope;
   measuring the first reflective side of the object by the first confocal microscope at a first position and measuring the second reflective side of the object by the second confocal microscope at a second position; and
   calibrating the first confocal microscope and the second confocal microscope based on the measurements of the first reflective side and the second reflective side at the first and second positions.

2. The method of claim 1, further comprising:
   establishing a first pathway in operative communication with the first confocal microscope and a second pathway in operative communication with the second confocal microscope;
   splitting a light beam into a first divided light beam and a second divided light beam;
   launching the first divided light beam through the first pathway and the second divided light beam through the second pathway;
   collimating the first divided light beam and the first collimated light beams into a plurality of first collimated light beams and a plurality of second collimated light beams; and
   focusing the plurality of second collimated light beams onto the first reflective surface for generating a plurality of first reflected light beams and focusing the plurality of second collimated light beams onto the second reflective surface for generating a plurality of second reflected light beams.

3. The method of claim 2, further comprising:
   detecting the signal generated by the plurality of first reflected light beams and the plurality of second reflected light beams; and
   measuring the intensity of each signal for determining the position of the first reflective side and the position of the second reflective side.

4. The method of claim 3, wherein calibrating the first confocal microscope and the second confocal microscope comprises calibrating a working distance between the first focusing lens and the second focusing lens.

5. The method of claim 4, wherein the working distance between the first focusing lens and the second focusing lens is calculated using the following equation:

$$L = F_1 + |x_{20} - x_{10}| + t_0 + F_2 \tag{1}$$

wherein L is the working distance between the first focusing lens and the second focusing lens; $F_1$ is the focal length of the first focusing lens; $F_2$ is the focal length of the second focusing lens; $t_0$ is known thickness of an object; $x_{20}$ is the position of the second focusing lens; and $x_{10}$ is the position of the first focusing lens.

6. The method of claim 2, wherein aligning the first confocal microscope with the second confocal microscope along the beam axis comprises aligning the first pathway with the second pathway such that the plurality of the first and second reflected light beams are aligned relative to the beam axis.

7. The method of claim 5, further comprising:
calculating working distance using the following equation:

$$L = F_1 + 1x_2 - x_1 1 + t_s + F_2 \qquad (2)$$

wherein L is the working distance; $F_1$ is the focal length of the first focusing lens, $F_2$ is the focal length of the second focusing lens; $t_s$ is unknown thickness value for the second object having a first side and an opposite second side; $x_1$ is a position of the first side of the first object; and $x_2$ is a position of the second side of the second object.

8. : The method of claim 7, further comprising: comparing the equation (1) and the equation (2) to obtain the following expression for calculating the thickness of the second object: $n_s = [NA^2 + (1 - NA^2)(t_s/d)^2]^{1/2}$.

9. The method of claim 8, further comprising:
determining a refractive index using the following equation:

$$n_s = [NA^2 + (1 - NA^2)(t_s/C)^2]^{1/2} \qquad (4)$$

wherein d is the distance between locations $x_0$ and $x_1$.

10. The method of claim 9, further comprising:
translating the second object along the beam axis between a first position and a second position relative to the first focusing lens.

11. The method of claim 10, further comprising:
translating the second object along the beam axis between a third position and a fourth position relative to the second focusing lens.

* * * * *